United States Patent
Byrnard et al.

(10) Patent No.: US 7,922,986 B2
(45) Date of Patent: Apr. 12, 2011

(54) REAGENT CUP HOLDER

(75) Inventors: Allan Byrnard, Ishoj (DK); Henrik Sandberg, Copenhagen K (DK)

(73) Assignee: Radiometer Medical ApS, Brønshøj (DK)

( * ) Notice: Subject to any disclaimer, the term of this patent is extended or adjusted under 35 U.S.C. 154(b) by 201 days.

(21) Appl. No.: 12/076,231

(22) Filed: Mar. 14, 2008

(65) Prior Publication Data

US 2008/0226508 A1   Sep. 18, 2008

Related U.S. Application Data

(60) Provisional application No. 60/935,645, filed on Aug. 23, 2007.

(30) Foreign Application Priority Data

Mar. 16, 2007  (EP) .................................... 07388016

(51) Int. Cl.
*B01L 9/00*    (2006.01)
*B01L 3/00*    (2006.01)
*B01L 99/00*   (2006.01)
*G01N 21/75*   (2006.01)
*G01N 31/22*   (2006.01)
*G01N 33/52*   (2006.01)

(52) U.S. Cl. ........ 422/561; 422/425; 422/547; 422/560; 422/565; 422/570

(58) Field of Classification Search .......... None
See application file for complete search history.

(56) References Cited

U.S. PATENT DOCUMENTS

| | | | | |
|---|---|---|---|---|
| 5,441,895 A | * | 8/1995 | Jakubowicz et al. | 422/102 |
| 5,510,266 A | * | 4/1996 | Bonner et al. | 221/88 |
| 5,632,410 A | * | 5/1997 | Moulton et al. | 221/79 |
| 6,106,783 A | * | 8/2000 | Gamble | 422/102 |
| 6,149,872 A | * | 11/2000 | Mack et al. | 422/102 |
| 6,429,026 B1 | | 8/2002 | Petterson et al. | |
| 6,551,833 B1 | | 4/2003 | Lehtinen et al. | |
| 7,569,187 B2 | * | 8/2009 | Schabbach et al. | 422/64 |
| 2003/0059350 A1 | * | 3/2003 | Sacherer | 422/104 |
| 2004/0161788 A1 | | 8/2004 | Chen et al. | |
| 2004/0241042 A1 | * | 12/2004 | Pugia et al. | 422/58 |
| 2005/0136546 A1 | * | 6/2005 | Berndt et al. | 422/102 |
| 2006/0188404 A1 | * | 8/2006 | Gjerde | 422/99 |
| 2006/0245972 A1 | | 11/2006 | Osone et al. | |

* cited by examiner

*Primary Examiner* — Jill Warden
*Assistant Examiner* — Charles Hammond
(74) *Attorney, Agent, or Firm* — Morgan, Lewis & Bockius LLP

(57) ABSTRACT

A reagent cup device 1 includes a plurality of individually sealed reagent cup compartments 7, each holding a reagent cup 8 having an open end and an inner surface, at least part of which is coated with a chemical reagent. Each reagent cup compartment 7 is closed and has a first end covered by a first breakable seal 5 and a second end covered by a second breakable seal 10. Since the reagent cup compartments 7 are individually sealed by the breakable seals 5, 10, it is possible to gain access to the interior of a reagent cup compartment 7, and thereby to the reagent cup 8 held therein, without breaking the sealing of the remaining reagent cup compartments 7. Thereby degradation of the chemical reagent in the reagent cups 8 is reduced, and the expected lifetime of the reagent cups 8 is accordingly increased. The breakable seals 5, 10 may be provided with weakened zones in order to easier break the seals 5, 10 when access is desired.

17 Claims, 6 Drawing Sheets

REAGENT CUP HOLDER

The present application claims the benefit of priority of U.S. Provisional Application No. 60/935,645, filed on Aug. 23, 2007, which is incorporated by reference in its entirety, and the benefit of priority of European Patent Application No. 07388016.3, filed on Mar. 16, 2007, which is incorporated by reference in its entirety.

The present invention relates to a device for holding a plurality of reagent cups, in particular reagent cups of the kind which may be used in an apparatus for analyzing biological samples, such as blood samples. More particularly, the present invention relates to a device as defined above, and which is suitable for being positioned in such an apparatus.

Various apparatuses for performing analysis of biological samples, such as blood samples, are known. When a sample is to be analyzed, e.g. with respect to a specific parameter, it is often supplied to a reagent cup containing a chemical reagent which is relevant with respect to the specific parameter. In order to prevent degradation of the chemical reagent, it is preferred that the reagent cups are stored under sealed conditions. Furthermore, in order to easily position a plurality of reagent cups in an analyzing apparatus, a plurality of reagent cups may be arranged in a holder, such as a cassette, and the entire holder including the plurality of reagent cups is sealed. However, in order to retrieve one reagent cup from the holder, the seal must be broken, and thereby the remaining reagent cups in the holder will no longer be stored under sealed conditions, and the expected lifetime of these reagent cups, in particular of the chemical reagent contained therein, is reduced considerably.

U.S. Pat. No. 6,551,833 discloses a diagnostic measuring device comprising a cassette drum on the circumference of which sample cup cassettes containing sample cups have been placed. The sample cups from the sample cup cassettes may be fed to a handling drum by means of gravity. In order to obtain this, the sample cups are arranged in the sample cup cassette in a vertical stack. Thus, the sample cup cassette and each of the sample cups arranged therein are sealed together, and the sealing for all of the sample cups is broken if a single sample cup is to be fed to the handling drum. Accordingly, the problems described above occur.

It is, thus, an object of the invention to provide a reagent cup device for holding a plurality of reagent cups, in which the expected lifetime of each of the reagent cups is increased as compared to prior art reagent cup devices.

It is a further object of the invention to provide a reagent cup device for holding a plurality of reagent cups, in which easy access to each of the reagent cups is possible without compromising the expected lifetime of the reagent cups.

According to a first aspect of the invention, the above and other objects are fulfilled by providing a reagent cup device comprising:

a plurality of individually sealed reagent cup compartments, wherein each reagent cup compartment is closed and has a first end being covered by a first breakable seal, and a second end being covered by a second breakable seal, each compartment holding a reagent cup having an open end and an inner surface at least part of which is coated with a chemical reagent.

The reagent cup device comprises a plurality of reagent cup compartments, and each reagent cup compartment holds a reagent cup. Accordingly, the reagent cup device holds a plurality of reagent cups, and a plurality of reagent cups may thereby be inserted in an analysis apparatus by inserting a single reagent cup device.

Each reagent cup has an open end and an inner surface. At least part of the inner surface is coated with a chemical reagent. In the present context the term 'chemical reagent' should be interpreted to mean a substance in dry form which reacts with a sample, e.g. a blood sample, supplied to the reagent cup if the sample contains a specific biochemical marker. The chemical reagent may advantageously comprise a fluorescent lanthanide chelate label which may at a later point in the analysis process serve as a basis for a time resolved fluorescence analysis. In this case the result of the time resolved fluorescence analysis gives a quantitative indication of the level of the specific biochemical marker in the sample. Suitable chemical reagent systems are described in U.S. Pat. No. 6,429,026.

The reagent cups may advantageously be coated with an absorbing material in which the chemical reagent may be absorbed.

The reagent cup compartments are individually closed or sealed, there being no fluid communication between any of the reagent cup compartments. Accordingly, access may be gained to the interior of each of the reagent cup compartments without gaining access to any of the other reagent cup compartments and without breaking the sealing of any of these. Since the reagent cups are held in the reagent cup compartments, this means that access may be gained to each of the reagent cups without breaking the sealing protecting any of the other reagent cups. This is very advantageous, since it allows a user to use one of the reagent cups for analysis purposes without compromising the expected lifetime of the remaining reagent cups of the device. Simultaneously, a device holding a plurality of reagent cups is provided, and the advantages related thereto, such as easy insertion of a plurality of reagent cups in the analysis apparatus, availability of relevant reagent cups when a sample is introduced in the analysis apparatus, etc., is thereby also obtained.

Each reagent cup compartment has a first end being covered by a first breakable seal, and a second end being covered by a second breakable seal. Since the seals are breakable, it is possible to gain access to the interior of a reagent cup compartment, and thereby to the reagent cup stored therein, via one of the seals. Furthermore, in the case that the breakable seals are arranged opposite to each other, it is even possible to introduce a punching head into a desired reagent cup compartment via one of the breakable seals, and punch the corresponding reagent cup out of the reagent cup compartment via the other breakable seal, using the punching head. This will be described further below.

Each of the reagent cups may be arranged loosely in a reagent cup compartment. In this manner, the reagent cups are unsecured to the reagent cup compartment and may thus easily be removed therefrom, e.g. upon breakage of one of the seals.

Each of the reagent cup compartments may be individually spaced from each of the other reagent cup compartments. In the present context the term 'individually spaced from each other' means that none or only a small part of the total wall surface of a given reagent cup compartment also forms part of the total wall surface of one of the other reagent cup compartments. Thus, according to this embodiment, the majority of the total wall surface of a given cup cartridge compartment is not shared with another cup cartridge compartment, i.e. the majority of the wall surface is not arranged adjacent to or forms a boundary to another cup cartridge compartment. Preferably, less than 10% of the total wall surface, such as between 5% and 10% of the total wall surface of a given reagent cup compartment is shared with another reagent cup compartment.

This construction considerably reduces permeability to moisture, i.e. it is possible to keep the interior of the reagent cup compartments very dry. In particular, this construction prevents moisture from entering a sealed reagent cup compartment arranged next to a reagent cup compartment in which the sealing has been broken. If the reagent cup compartments are not spaced from each other, there is a risk that moisture enters a sealed compartment via a common wall part between the sealed reagent cup compartment and a neighboring reagent cup compartment which is no longer sealed.

The reagent cup device may further comprise a frame part having a frame part wall, the frame part holding the plurality of reagent cup compartments. In this case, the frame part wall may advantageously define an outer boundary of the reagent cup device.

The frame part wall and the reagent cup compartments may be spaced apart. This construction also protects the reagent cups arranged in the sealed reagent cup compartments with respect to moisture, since moisture would have to diffuse through the frame part wall as well as through a wall of a reagent cup compartment in order to enter the reagent cup compartment.

The frame part may be covered by at least one breakable seal, and the breakable seal(s) of the frame part may be integrated with the first and/or the second breakable seal of the reagent cup compartments. According to this embodiment, the reagent cup device may advantageously be covered by two breakable seals, one covering a first end of each of the reagent cup compartments as well as a first end of the frame part, and another one covering a second end of each of the reagent cup compartments as well as a second end of the frame part. In this case it should be ensured that sufficient attachment of the breakable seals around the reagent cup compartments is provided in order to obtain individual sealing of each of the reagent cup compartments. As an alternative, individual breakable seals may be provided for the reagent cup compartments and one or more additional seals may be provided for the frame part.

The frame part may be made from a polymer material, such as a suitable cyclic olefin copolymer (COC), preferably the material Topas® from the company Topas Advanced Polymers. Topas® is a very suitable material for this purpose because it has a very low permeability to moisture, and it is thereby possible to keep the interior of the reagent cup device relatively dry when the frame part is made from Topas®. As an alternative, other suitable polymer materials may be used, e.g. high density polyethylene (HDPE), polystyrene (PS), polystyrene-polyethylene (PS-PE) or liquid crystalline polymer (LCP).

At least an outer part of the frame part may be provided with a coating of a metallic material. This also reduces the permeability to moisture of the frame part. The metallic material may, e.g., be or comprise aluminum, gold, stainless steel or any other suitable metallic material. Aluminum is very suitable for the purpose.

The reagent cup compartments may be arranged in a two-dimensional pattern. This construction makes it very easy to individually access each of the reagent cup compartments without breaking the sealing of any of the other reagent cup compartments.

The first breakable seal and/or the second breakable seal may be provided with one or more weakened zones. Such weakened zones make it easier to break the seals when desired, and it may further be ensured that the relevant seal is broken in an intended manner, e.g. without affecting the breakable seals of a neighboring reagent cup compartment, tearing in an intended direction and/or in an intended pattern, etc. According to one embodiment the breakable seals of a reagent cup compartment are arranged opposite to each other. When it is desired to use the reagent cup arranged in the reagent cup compartment for analysis purposes a punching head is entered into the reagent cup compartment via one of the breakable seals, the punching head preferably being capable of cutting through this breakable seal. The punching head then punches the reagent cup through the other breakable seal. In many cases the reagent cup will have a substantially flat bottom in order to allow the reagent cup to stand upright inside an analysis apparatus during analysis of a sample applied to the reagent cup. Accordingly, it may require a relatively large force by the punching head in order to punch the reagent cup through the breakable seal. However, the required force may be reduced considerably by providing a weakened zone to the breakable seal through which the reagent cup is to be punched.

The weakened zone(s) may have been provided by a laser cutting technique. According to this embodiment a small part of the material of the breakable seal(s) is removed by means of a laser, e.g. in a cross-like pattern, without penetrating the seal(s).

The reagent cup device may further comprise at least one drying element. One or more drying elements may be arranged inside the reagent cup device, but outside the reagent cup compartments, e.g. between the reagent cup compartments. Alternatively or additionally, at least one of the reagent cup compartments may hold a drying element. Drying elements ensure that if moisture should enter the reagent cup device, despite attempts to avoid this, the chemical reagent arranged in the reagent cups may still be kept dry. This increases the expected lifetime of the reagent cups, in particular of the chemical reagent contained therein. Arranging one or more drying elements between the reagent cup compartments ensures that even if the seal of one reagent cup compartment is broken and moisture diffuses through the walls of that reagent cup compartment into the interior of the reagent cup device, this moisture is prevented from entering the other reagent cup compartments via their respective walls. Preferably, the drying element comprises silica gel, but other suitable materials may be used such as molecular sieves, paper or different kinds of clay.

The first breakable seal and/or the second breakable seal may be made from a metal or an alloy, preferably from aluminum or from an alloy of aluminum. An aluminum laminate may advantageously be used, e.g. aluminum blister foil or a laminate of polyester, aluminum and polyethylene, such as a PETP/Al/PE laminate. Alternatively, any other suitable metal, alloy and/or laminate may be used, or a suitable non-metallic material may be used. When the breakable seal is made from a laminate, the weakened zone(s) may be provided in one of the layers only.

The reagent cup compartments may be made from a polymer material, such as a suitable cyclic olefin copolymer (COC), preferably the material Topas® from the company Topas Advanced Polymers. Topas® is a very suitable material for this purpose because it has a very low permeability to moisture, and it is thereby possible to keep the interior of the reagent cup compartments relatively dry when the reagent cup compartments are made from Topas®. As an alternative, other suitable polymer materials may be used, e.g. high density polyethylene (HDPE), polystyrene (PS), polystyrene-polyethylene (PS-PE) or liquid crystalline polymer (LCP). In the case that the reagent cup device comprises a frame part as described above, the frame part and the reagent cup compartments may advantageously form an integral part made from the same material.

The reagent cups may be made from a polymer material, preferably from polystyrene (PS). Alternatively, another suitable polymer material may be used.

According to a second aspect of the invention the above and other objects are fulfilled by providing a method of operating a reagent cup device according to any of the preceding claims, the method comprising the steps of:

providing a punching head comprising:

a cutting part adapted for cutting a breakable seal, and a punching part adapted for punching a reagent cup from a corresponding reagent cup compartment, cutting a first breakable seal of a reagent cup compartment using the cutting part of the punching head, and punching a reagent cup arranged in said reagent cup compartment through the second breakable seal of said reagent cup compartment using the punching part of the punching head.

It should be noted that a person skilled in the art would readily recognize from the description herein that any feature described in combination with the first aspect of the invention could equally be combined with the second aspect of the invention, and vice versa.

The breakable seals are preferably arranged opposite to each other as described above, thereby allowing the punching head to perform the steps of cutting and punching in a single substantially linear movement.

The cutting part of the punching head is preferably relatively sharp in order to allow the cutting part to cut through the first breakable seal, even if the first breakable seal is not provided with one or more weakened zones.

The punching part of the punching head is rounded. Thereby it is adapted to punch a reagent cup through the second breakable seal without causing damage to the reagent cup or to a chemical reagent contained therein. For example, the punching part of the punching head may push against an upper surface of the reagent cup during the punching step. Thereby it is prevented that the punching head gets into contact with a dry chemical reagent arranged in a bottom part of the reagent cup, and the risk of damaging the chemical reagent is thereby minimized. As described above, the reagent cup may advantageously be punched through a weakened zone of the second breakable seal.

The punching head may be moved along a substantially vertical direction during the cutting step and during the punching step. Thereby a reagent cup may be moved partly by means of gravity when it has been punched through the second breakable seal by the punching head.

BRIEF DESCRIPTION OF THE DRAWINGS

The accompanying drawings, which are incorporated in and constitute a part of this specification, illustrate embodiments of the invention and together with the description serve to explain the principles of the invention. In the drawings.

DESCRIPTION OF PREFERRED EMBODIMENTS

Figure 1:
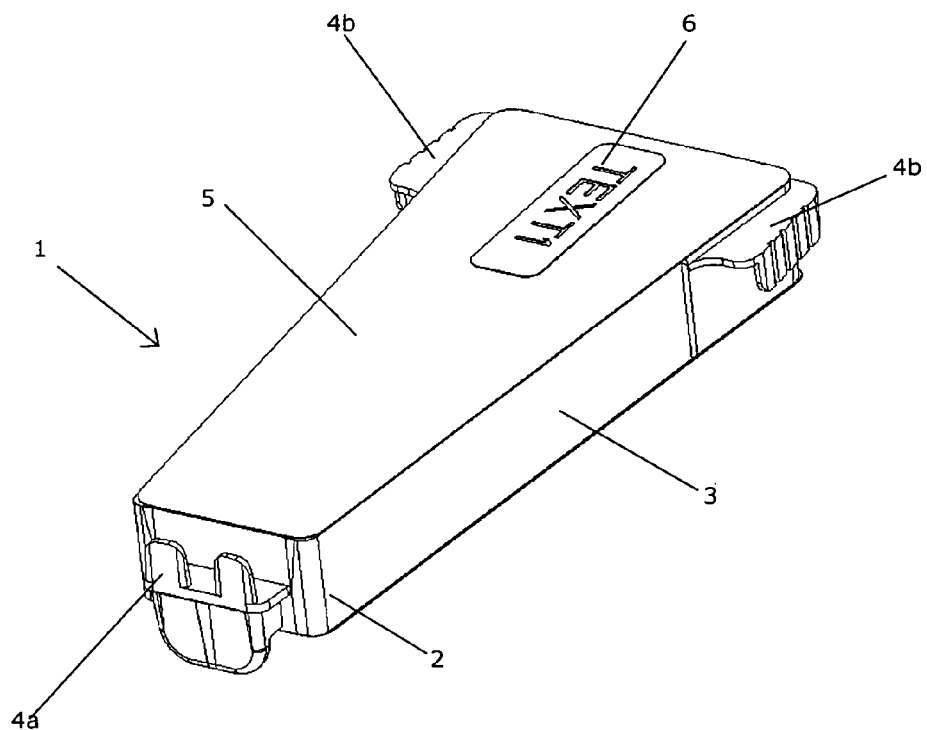
FIG. 1 is a perspective view of a reagent cup device according to an exemplary embodiment of the invention.

FIG. 1 is a perspective view of a reagent cup device 1 according to an embodiment of the invention. The reagent cup device 1 comprises a frame part 2 having an outer wall 3 defining an outer boundary for the reagent cup device 1. Holding parts 4a, 4b are arranged on the outer wall 3 of the frame part 2. The holding part 4a is used for guiding the reagent cup device 1 inside an analysis apparatus. The analysis apparatus may hold a number of reagent cup devices, e.g. reagent cups devices with reagent cups containing various chemical reagents for different analysis. The holding parts 4b are used for allowing an operator to hold the reagent cup device 1, e.g. while inserting the reagent cup device 1 in an apparatus.

The upper part of the reagent cup device 1 is provided with a first breakable seal 5 sealing the entire interior of the reagent cup device 1, as well as individually sealing each of a plurality of reagent cup compartments (not visible) arranged inside the reagent cup device 1. The lower part of the reagent cup device 1 is similarly provided with a second breakable seal (not visible), also sealing the interior of the reagent cup device 1, as well as individually sealing each of the reagent cup compartments.

The first breakable seal 5 is provided with a label 6 which may contain information relating to the kind of chemical reagent contained in the reagent cups of the reagent cup device 1. The information may be in the form of visual information, such as a text message or a color code, and/or in the form of a machine readable code, such as a bar code or a transponder.

Figure 2:
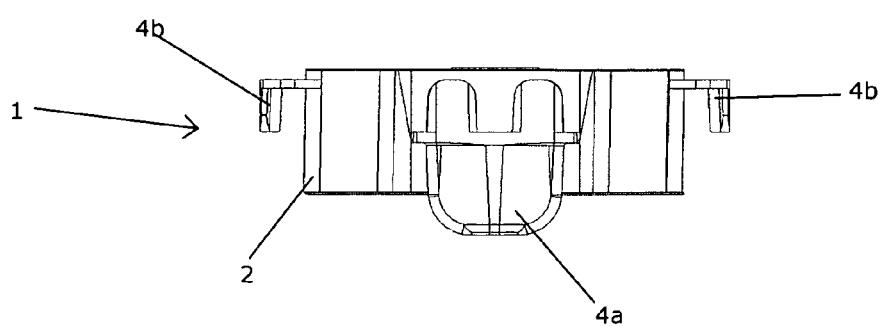
FIG. 2 is an end view of the reagent cup device of FIG. 1.
Figure 3:
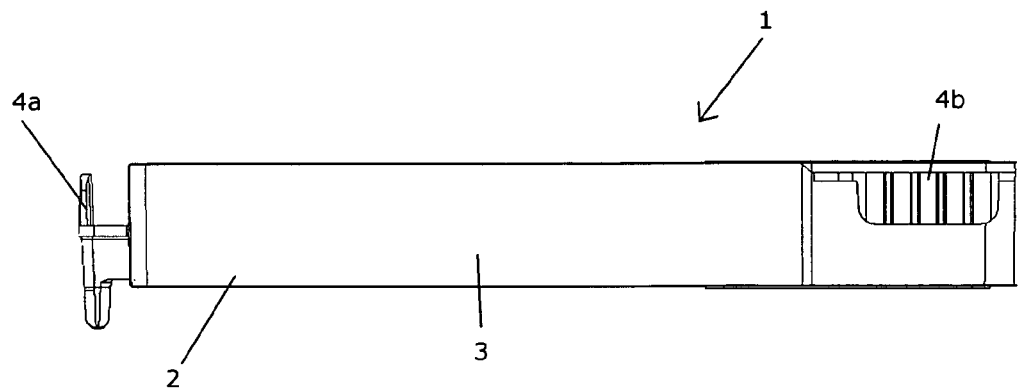
FIG. 3 is a side view of the reagent cup device of FIGS. 1 and 2.

FIG. 2 is an end view of the reagent cup device 1 of FIG. 1, and FIG. 3 is a side view of the reagent cup device 1 of FIGS. 1 and 2. In FIGS. 2 and 3 the holding parts 4a, 4b are clearly seen.

Figure 4:
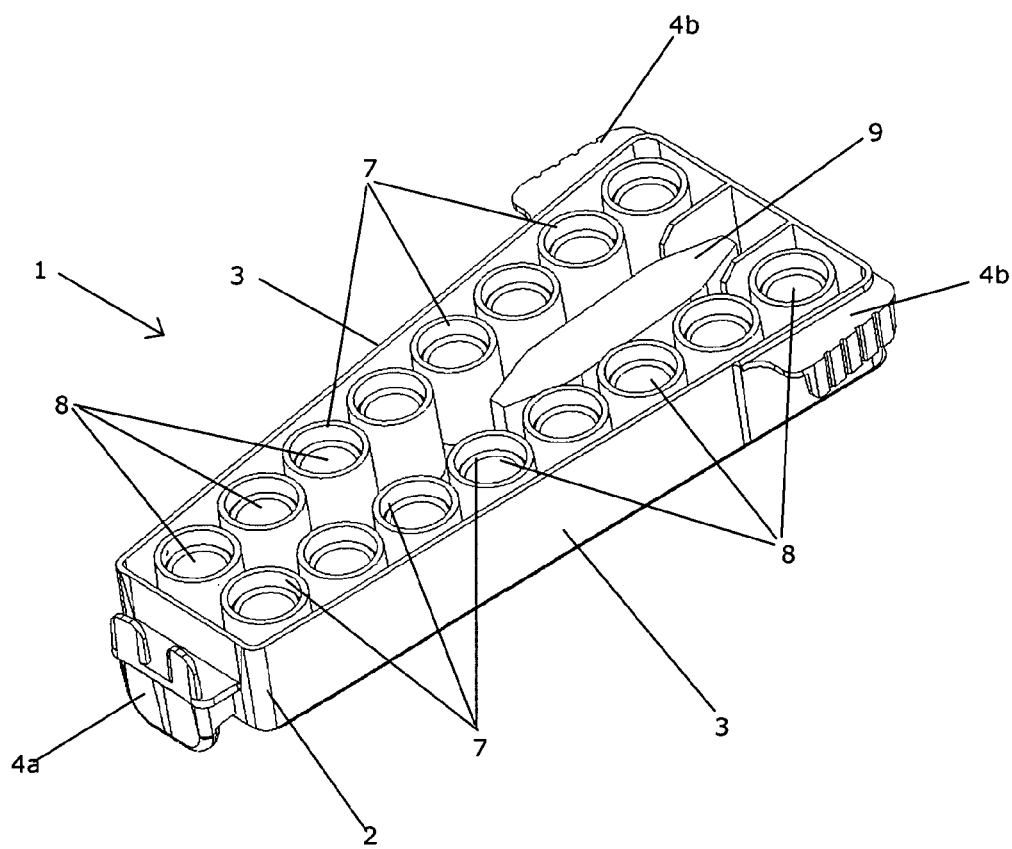
FIG. 4 is a perspective view of the reagent cup device of FIGS. 1-3 with a breakable seal removed.

FIG. 4 is a perspective view of the reagent cup device 1 of FIGS. 1-3. In the reagent cup device 1 of FIG. 4, the first breakable seal has been removed, thereby revealing the interior of the reagent cup device 1. Thus, it may be seen that the reagent cup device 1 comprises sixteen reagent cup compartments 7, each holding a reagent cup 8. In a space defined between the reagent cup compartments 7, a drying element 9 is arranged in order to ensure that the interior of the reagent cup device 1 is kept dry.

The reagent cup compartments 7 are arranged spaced apart from each other and from the outer wall 3 of the frame part 2. As described above, this reduces the permeability to moisture, and it is thereby easier to keep the reagent cups 8 dry.

Figure 5:
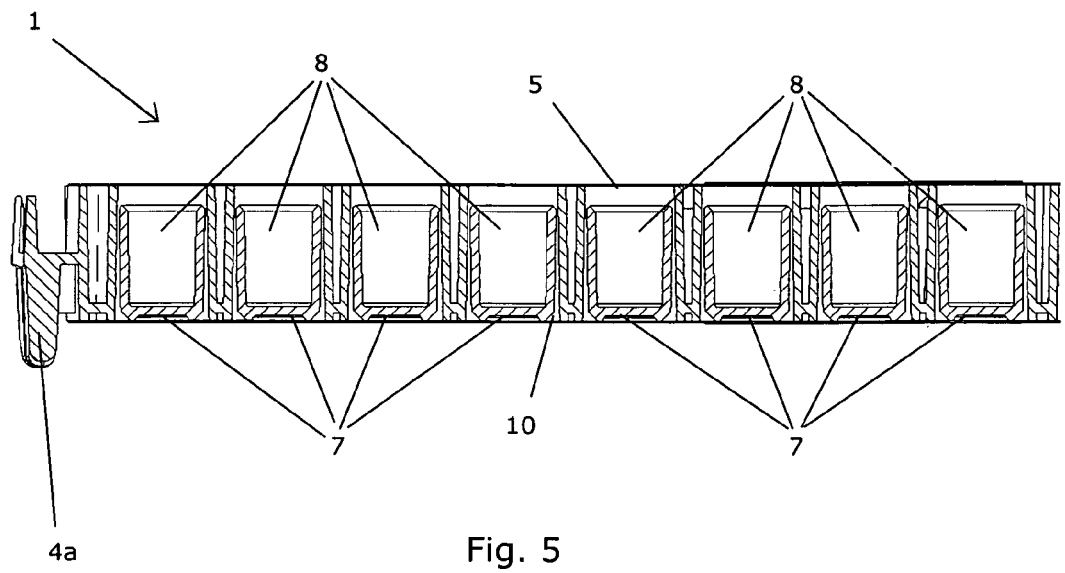
FIG. 5 is a cross sectional view of the reagent cup device of FIGS. 1-4.

FIG. 5 is a cross sectional view along a longitudinal direction of the reagent cup device 1 of FIGS. 1-4. In FIG. 5 it is clearly seen how the reagent cups 8 are arranged in the reagent cup compartments 7. As indicated in the figure, the reagent cups 8 are arranged loosely in the compartments 7, the cups 8 being unsecured to the walls of the compartments 7. Furthermore, the first breakable seal 5 as well as the second breakable seal 10 is visible, the seal 5 being sealed to the entire upper rim of each of the individual reagent cup compartments 7 and the seal 10 being sealed to the entire lower rim of each of the individual reagent cup compartments 7, thus individually closing each reagent cup compartment 7.

When it is desired to use a reagent cup 8 of the reagent cup device 1 for analysis purposes, the first breakable seal 5 may be broken by means of a punching head at a position corresponding to one of the reagent cup compartments 7. The punching head may then punch the reagent cup 8 through the second breakable seal 10. Thereby, the reagent cup 8 has been punched out of the reagent cup compartment 7 without breaking the sealing of the remaining reagent cup compartments 7.

Figure 6:
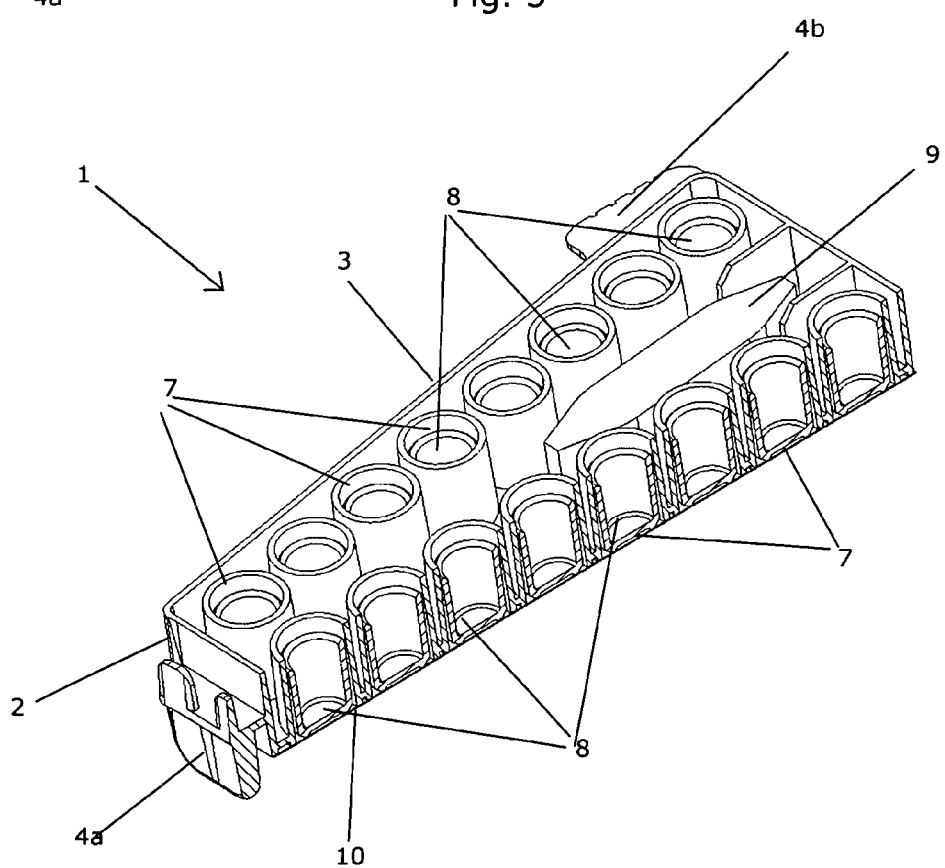
FIG. 6 is a perspective view of the reagent cup device of FIGS. 1-5 with a part removed.

FIG. 6 is a perspective view of the reagent cup device 1 of FIGS. 1-5. In FIG. 6 a part of the reagent cup device 1 has been removed, thereby showing the cross sectional cut of FIG. 5.

As can be seen from FIGS. 5 and 6, the reagent cup compartments 7 are individually sealed from each other, there being no air or fluid communication between any of the reagent cup compartments 7.

Figure 7:
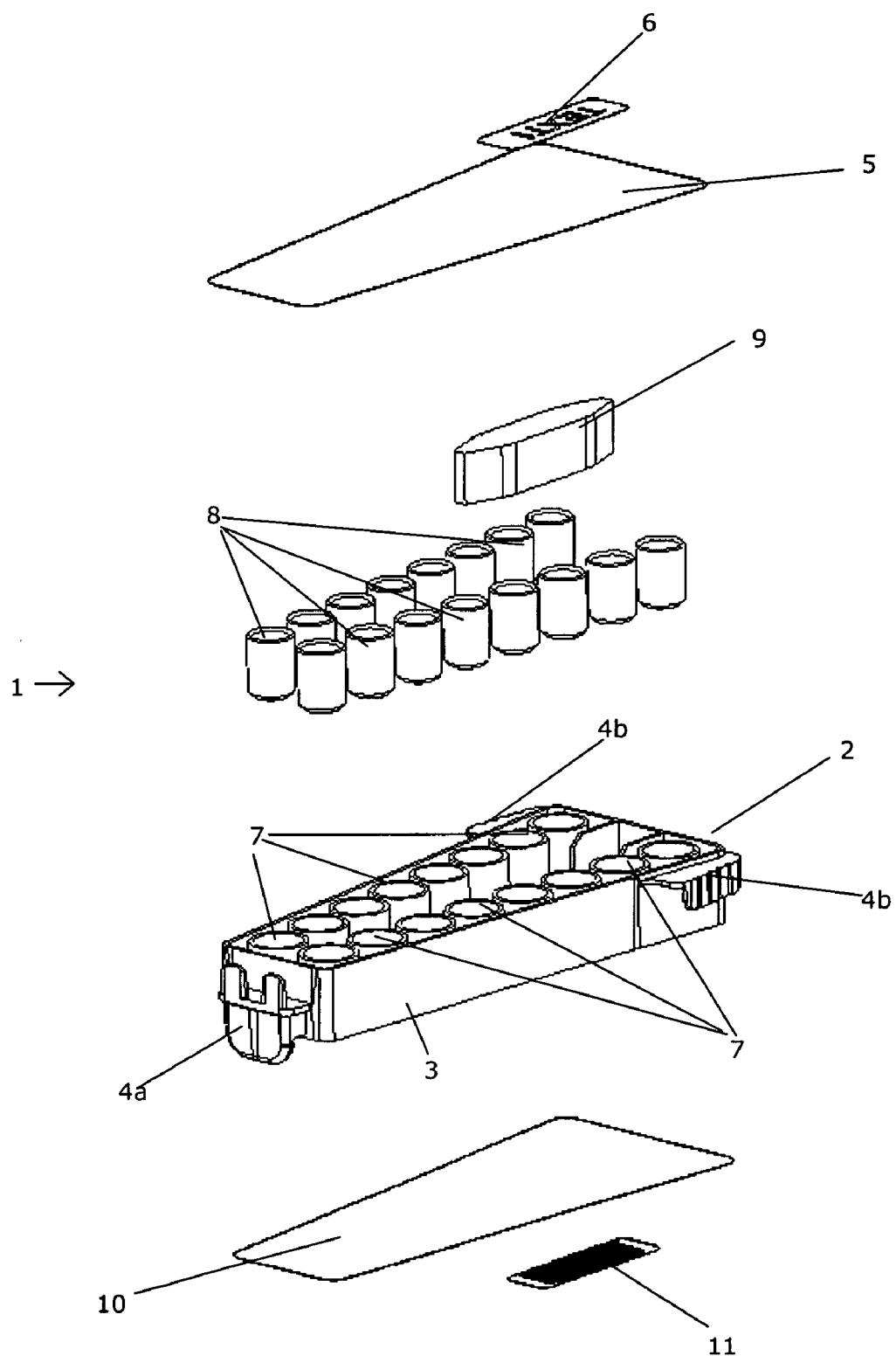
FIG. 7 is an exploded view of the reagent cup device of FIGS. 1-6, and FIGS. 8-11 illustrate an exemplary punching device for use in performing a method according to an embodiment of the invention.

FIG. 7 is an exploded view of the reagent cup device 1 of FIGS. 1-6. Thus, the individual parts of the reagent cup device 1 may be clearly seen in FIG. 7. Furthermore, an additional label 11 may be seen. The additional label 11 is normally attached to the second breakable seal 10.

In the exemplary embodiment shown in the FIGS. 1-7, the frame part 2, the holding parts 4a, 4b and the cup compartments 7 may all be injection molded in one piece of the material Topas® COC from the company Topas Advanced Polymers. The reagent cups 8 in the cup compartments 7 may be made of polystyrene (PS). The drying element 9 comprises a bag containing 1 gram of silica gel. Both breakable seals 5 and 10 are made, for example, from laminates comprising an outer layer of polyester, a middle layer of aluminum and an inner layer of polyethylene. The seals 5, may be heat welded to the circumference of the wall 3 of the frame part 2 as well as to the circumference of each cup compartment 7. Thus, each cup compartment 7 as well as the interior of the frame part 2 is individually sealed from the ambiance and from the other cup compartments 7. In the bottom of each cup compartment 7, the breakable seal 10 has a weakened zone provided, for example, by removing a small part of the inner polyethylene layer in a cross-like pattern by means of a laser. The weakened zone is provided without penetrating the seal.

Figure 8:
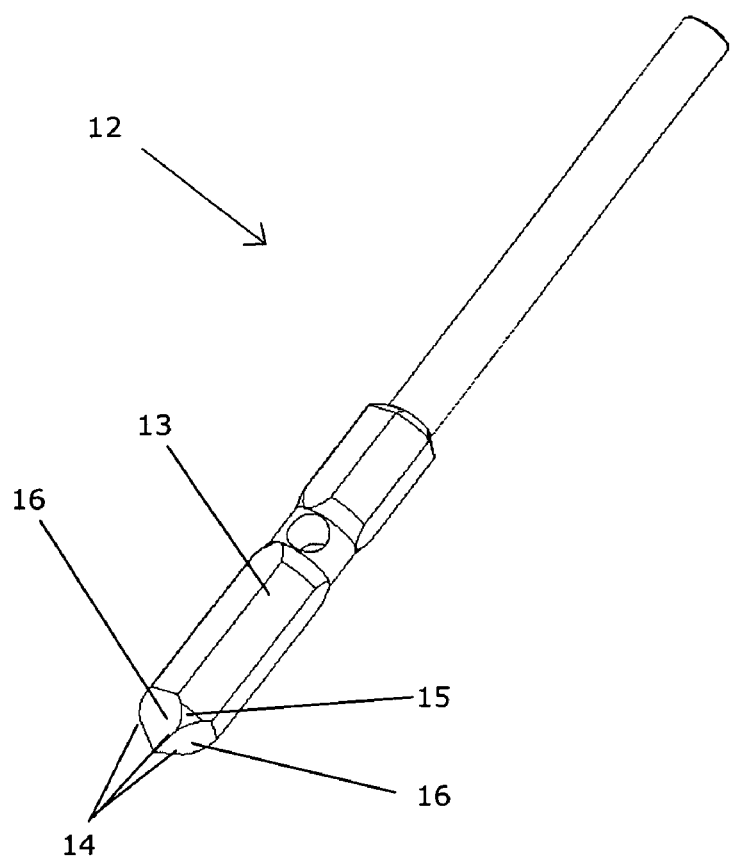

FIG. 8 is a perspective view of an exemplary punching device 12 for use in performing a method according to an embodiment of the invention. The punching device 12 is provided with a punching head 13 arranged at one end of the punching device 12. The punching head 13 comprises three sharp edges 14 formed as the intersections between three concave portions 16, and three rounded portions 15, one of which is visible in FIG. 8. The three sharp edges 14 meet in a point at the center of the punching head 13 and constitute a cutting part thereof and the three rounded portions 15 constitute a punching part of the punching head 13.

The punching device 12 is adapted to be arranged in an apparatus for analyzing samples, where the apparatus is adapted to contain one or more reagent cup devices according to the invention. The punching device 12 is arranged in the apparatus in a substantially vertical manner with the punching head 13 facing downwards. The punching device 12 is operated in the following manner.

When it is desired to use a reagent cup of a reagent cup device for the purpose of analyzing a sample, the part of the reagent cup device where the reagent cup is positioned, is arranged immediately below the punching head 13. The punching device 12 is then moved in a substantially downwards direction. This causes the sharp edges 14 to cut through the first breakable seal of the reagent cup compartment holding the reagent cup, thereby breaking the sealing. The rounded portions 15 will then abut the upper edge of the reagent cup, and continued movement of the punching device 12 in a substantially downwards direction will thereby push the reagent cup against and through the second breakable seal. As mentioned above, the second breakable seal may advantageously comprises a weakened zone in order to allow the reagent cup to more easily break the seal during this punching procedure.

Since the rounded portions 15 abut the upper edge of the reagent cup, it is prevented that the sharp edges 14 of the punching head 13 reach the bottom part of the reagent cup, and thereby the risk of damaging a chemical reagent coated onto the bottom part is minimized.

Figure 9:
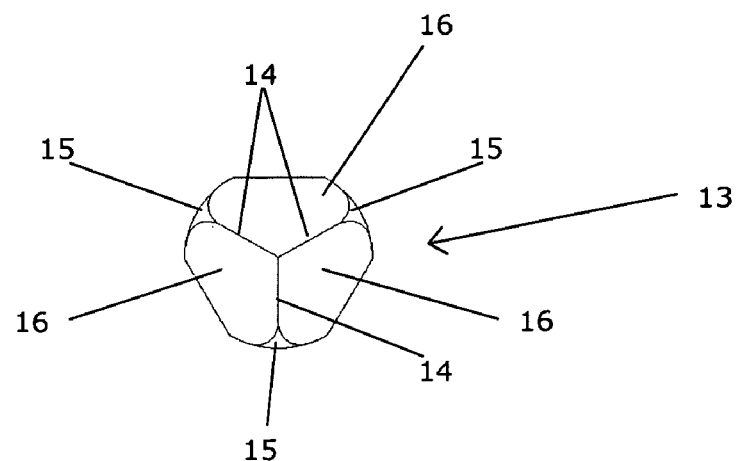

FIG. 9 is a view of the punching head 13 of the punching device 12 of FIG. 8 seen from below. The three sharp edges 14 and the three rounded portions 15 are clearly seen.

Figures 10, 11:
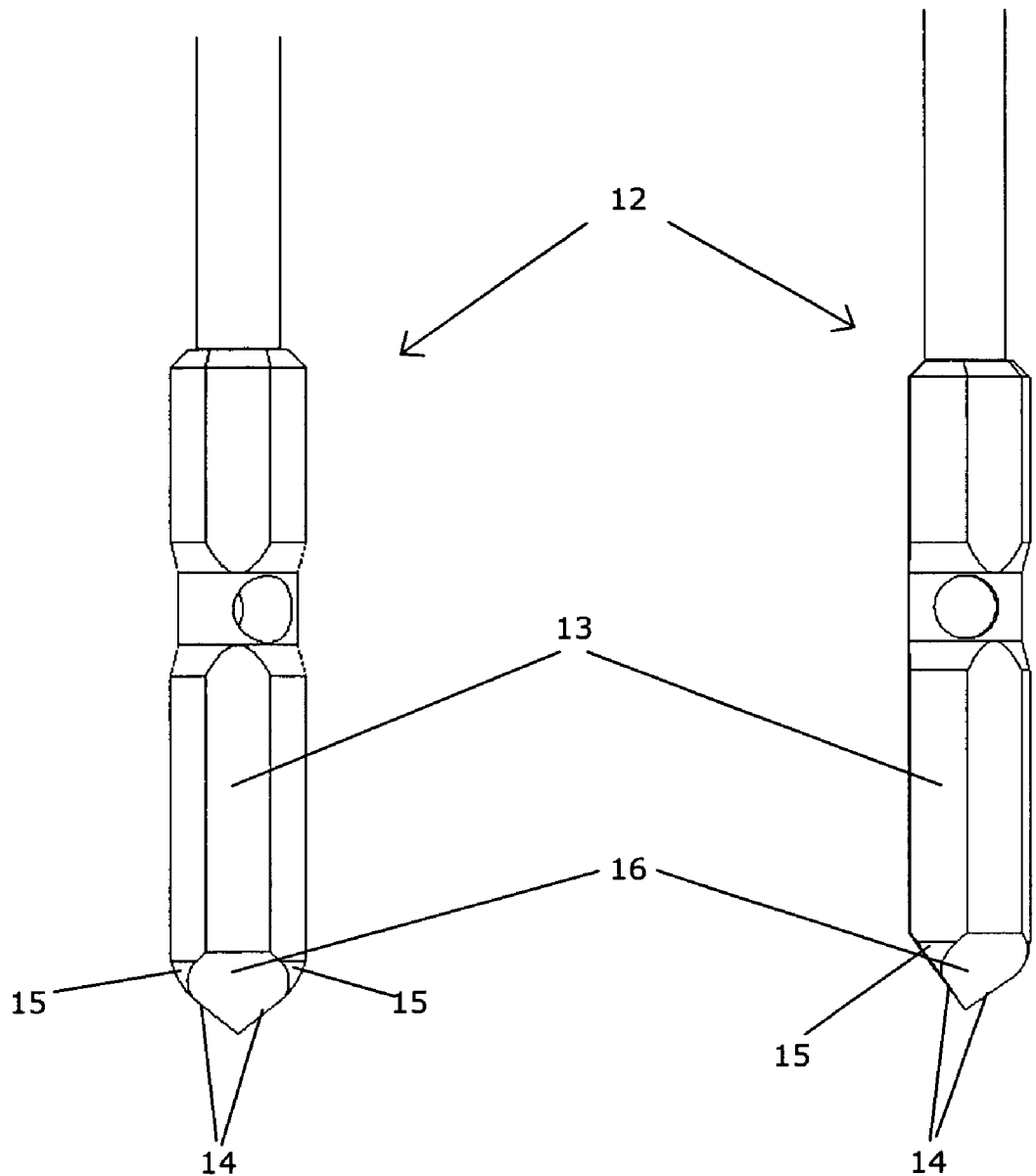

FIGS. 10 and 11 are side views of the punching device 12 of FIGS. 8 and 9 seen from two different angles. The relative positions of the sharp edges 14 and the rounded portions 15 may be seen.

It will be apparent to those skilled in the art that various modifications and variations can be made in the reagent cup holder and/or punching device of the present invention without departing from the spirit or scope of the invention. Thus, it is intended that the present invention cover the modifications and variations of this invention provided they come within the scope of the appended claims and their equivalents.

The invention claimed is:

1. A reagent cup device comprising:
    a frame part having a frame part wall defining an outer boundary for the reagent cup device and an interior thereof, the frame part having a plurality of individually spaced reagent cup compartments, each reagent cup compartment having a first end and a second end, and each reagent cup compartment holding a reagent cup, each reagent cup having an open end and an inner surface at least part of which is coated with a chemical reagent,
    wherein the frame part wall and the reagent cup compartments are spaced apart;
    wherein a first breakable seal covers the first end of each of the reagent cup compartments and a first end of the frame part, and a second breakable seal covers the second end of each of the reagent cup compartments and a second end of the frame part, and
    wherein a drying element is provided in a space defined between the reagent cup compartments within the interior of the reagent cup device.

2. A reagent cup device according to claim 1, wherein the frame part is made from a polymer material.

3. A reagent cup device according to claim 2, wherein the frame part is made from a cyclic olefin copolymer (COC).

4. A reagent cup device according to claim 1, wherein at least an outer part of the frame part is provided with a coating of a metallic material.

5. A reagent cup device according to claim 1, wherein the reagent cup compartments are arranged in a two-dimensional pattern.

6. A reagent cup device according to claim 1, wherein at least one of the first breakable seal and the second breakable seal is provided with one or more weakened zones.

7. A reagent cup device according to claim 6, wherein the one or more weakened zones comprise cuts.

8. A reagent cup device according to claim 1, wherein at least one of the first breakable seal and the second breakable seal comprises a metal.

9. A reagent cup device according to claim 8, wherein the at least one breakable seal comprises an alloy.

10. A reagent cup device according to claim 8, wherein the at least one breakable seal comprises aluminum.

11. A reagent cup device according to claim 10, wherein the at least one breakable seal comprises an aluminum alloy.

12. A reagent cup device according to claim 1, wherein the reagent cup compartments are made from a polymer material.

13. A reagent cup device according to claim 12, wherein the reagent cup compartments are made from a cyclic olefin copolymer (COC).

14. A reagent cup device according to claim 1, wherein the reagent cups are made from a polymer material.

15. A reagent cup device according to claim 14, wherein the reagent cups are made from polystyrene (PS).

16. A method of operating a reagent cup device according to claim 1, the method comprising the steps of:

providing a punching head comprising a cutting part and a punching part, cutting the first breakable seal of a at least one of the reagent cup compartments using the cutting part of the punching head, and punching the reagent cup held in said at least one reagent cup compartment through the second breakable seal of said reagent cup compartment using the punching part of the punching head.

17. A method according to claim 16, wherein the punching head is moved along a substantially vertical direction during the cutting step and during the punching step.

* * * * *